United States Patent [19]

Benayahu et al.

[11] Patent Number: 5,688,531
[45] Date of Patent: Nov. 18, 1997

[54] METHOD FOR REGULATING BONE FORMING CELLS

[75] Inventors: Dafna Benayahu, Herzlia; Shlomo Wientroub, Tel-Aviv, both of Israel

[73] Assignee: Ramot University Authority for Applied Research and Industrial Development, Ltd., Tel-Aviv, Israel

[21] Appl. No.: 363,354

[22] Filed: Dec. 23, 1994

[51] Int. Cl.$^6$ ............................................... A61K 35/28
[52] U.S. Cl. ....................................... 424/574; 435/240.2
[58] Field of Search ........................... 424/529, 574, 424/577; 435/240.2

[56] References Cited

U.S. PATENT DOCUMENTS

| | | | |
|---|---|---|---|
| 4,439,196 | 3/1984 | Higuchi | 604/892.1 |
| 4,447,224 | 5/1984 | DeCant, Jr. et al. | 604/67 |
| 4,447,233 | 5/1984 | Mayfield | 604/152 |
| 4,486,194 | 12/1984 | Ferrara | 604/308 |
| 4,487,603 | 12/1984 | Harris | 604/152 |

OTHER PUBLICATIONS

Ascenzi et al., "X–ray diffraction and electron microscope study of osteons during calcification" *X–ray Calcif. Tiss. Res.*, 35:133–143, (1978).

Benayahu et al., "Bone marrow–derived stromal cell line expressing osteoblastic phenotype in vitro and osteogenic capacity in vivo" *J. Cell. Physiol.* 140, 1–7 (1989).

Benayahu et al., "Subpopulations of marrow stromal cells share a variety of osteoblastic markers" *Calcif. Tissue Int.*, 49:202–207 (1991).

Benayahu et al. "Differential effects of retinoic acid and growth factors on osteoblastic markers . . . " *Journal of Cellular Biochemistry* 56:62–73 (1994).

Burnell et al., "Bone matrix and mineral abnormalities in postmenopausal osteoporosis" *Metabolism*, 31:1113–1120 (1982).

Canalis, "Regulation of bone remodeling" in *Primer on the Metabolic Bone Diseases and Disorders of Mineral Metabolism*2nd ed., editor Murray J. Favus, Raven Press, NY (1993).

Dunnill et al., "Quantitative histological studies on age changes in bone" *J. Pathol. Bacteriol.*, 94:275–291 (1967).

Earney and Earneym, "Geriatric Hematology" *J.Am. Geriatr. Sco.*, 20:174–177 (1972).

Eventov et al., "Osteopenia, hematopoiesis, and bone remodelling in iliac crest and femoral biopsies: . . . ". *Bone*, 12:1–6 (1991).

Fuji et al., "Aging of human bone and articular cartilage collagen" *Gerentology*, 22:363–370 (1976).

Labarca and Paigen, "A simple, rapid, and sensitive DNA assay procedure" *Anal. Biochem.*, 102:344–352 (1980).

Lanotte et al., "Clonal preadipocyte cell lines with different phenytypes derived from murine marrow stroma:. . . " *J. Cell. Physiol.* 111:177–186 (1982).

Martin et al., "Bone marrow fat content in relation to bone remodeling and serum chemistry . . . " *Calcif. Tissue Int.*, 46:189–194 (1990).

Martin et al., "Studies of skeletal remodeling in aging men" *Clin. Orthop. Rel. Res.*, 149:268–282 (1980).

Mazess, "On aging bone loss" *Clin. Orthop. Rel. Res.*, 165, 239–252 (1982).

Meunier et al.; "Physiological senile involution and pathological rarefaction of bone" *Clin. Endocrinol. Metab.*, 2:239–256 (1972).

Meunier et al., "Osteoporosis and the replacement of cell populations of the marrow by adipose tissue" *Clin. Orthop. Rel. Res.*, 80:147–154 (1971).

Mosmann, J. "Rapid colorimetric assay for cellular growth and survival: application to proliferation and cytotoxicity assays" *J. Immunol. Method.*, 66:55–63 (1983).

Orbant and Odselius, "The concentration of calcium and phosphorus in trabecular bone from the iliac crest" *Calcif. Tiss. Int.*, 39:8–10 (1986).

Owen and Friedenstein, in *Cell and Molecular Biology of Vertebrate Hard Tissue*, vol. 136 (ed. D Evered and S. Harnett), pp. 42–60. Ciba Fdn. Symp., John Wiley & Sons (1988).

Postlethwaite et al., "Lymphocyte modulation of fibroblast function in vitro: stimulation and inhibition" *J. Immunol.* 132:2470–2477 (1984).

Riggs et al., "Changes in bone mineral density of the proximal femur and spine wth aging" *J. Clin. Invest.* 70:716–723 (1982).

Robb and Jowsey, "Quantitative measurement of fractional bone volume using digital scanning videodensitometry" *Calcif. Tiss. Res.*, 25:265–272 (1978).

Schroder and Touqaard, "Age changes in the quantity of hematopoietic tissue" Acta Pathol. Microbiol Scand. Sec. A., 84:559–560 (1977).

Simmons et al., "Age–related changes in the human femoral cortex" *J. Orthop. Res.* 9:155–167 (1991).

Strandth and Norlen, "Distribution per volume bone tissue of calcium, phosphorus and nitrogen from individuals . . . " *Acta Orthop. Scand.*, 35:257–263.12 (1965).

Tabuchi et al., "Bone deficit in ovariectomized rats" *J. Clin. Invest.* 78:637–642 (1991).

Wronski et al., "Estrogen and disphosphonate treatment provide long–term protection against osteopenia" *J. Bone Mio. Res.*, 6:387–394 (1991).

Zipori, "Regulation of hemopoiesis by cytokines that restrict options for growth and differentiation" *Cancer Cells* 2:205–211 (1990).

Zhang et al., (1991) "Contribution of marrow stromal cells to the regulation of osteoblast proliferation in rats . . " *Bone and Mineral*, 13:201–215.

*Primary Examiner*—Jean C. Witz
*Attorney, Agent, or Firm*—Kohn & Associates

[57] ABSTRACT

Regulation factors and a method for modulating bone forming cells including the steps of collecting regulation factors from bone stromal cells including marrow adipocytes and treating the bone forming cells with the regulation factors derived from stromal cells to modify the bone forming cells.

5 Claims, 5 Drawing Sheets

METHOD FOR REGULATING BONE FORMING CELLS

BACKGROUND OF THE INVENTION

1. Technical Field

The present invention relates to a method for modulating, bone forming cells. More particularly, the present invention relates to a method and regulation factors for regulating bone forming cells by treating the bone forming cells with regulation factors derived from bone marrow adipocytes and other stromal cells.

2. Background Art

The topic of bone related disorders and diseases has gained considerable attention over the past years with a particular focus on osteoporosis. Throughout life, there is a constant remodeling of skeletal bone. In this remodeling process, there is a delicate balance between bone resorption by osteoclasts and subsequent restoration by osteoblasts. In osteoporosis it is thought that loss of bone density results from an imbalance in this delicate process.

While it is well known that bone matrix undergoes structural changes with aging, the nature of these changes has, yet, remained undetermined. The majority of studies on age-related changes in human bone have been directed towards either elucidating changes in bone on a morphological level (Ascenzi et al., 1978; Martin et al., 1982) or have sought to describe age-related changes by quantitatively comparing rates of bone loss (Mazess, 1982; Meunier et al., 1972; Riggs et al., 1982; Robb and Jowsey, 1978; Simmons et al., 1991).

Additionally, some studies have attempted to elucidate age-related chemical changes in the bone matrix (Burnell et al., 1982; Katsuyuki et al., 1976) or in the minerals included in the bone matrix (Orbant and Odselius, 1986; Strandh and Norlen, 1965).

A number of factors produced locally in bone are thought to participate in the remodeling process. (Kumar et al., *Basic Pathology*, 5th ed. 1992 pp. 682–683). Among these factors which may contribute to either osteoblastic or osteoclastic activity are cytokines such as interleukin 1 (IL- 1), IL-6, macrophage and granulocyte/macrophage colony stimulating factors, and tumor necrosis factor (TNF); platelet-derived growth factor (PDGF); transforming growth factor β (TGFβ); fibroblast growth factors (FGF); polypeptide hormones such as insulin, parathyroid hormone (PTH), growth hormone (GH), and calcitonin; steroids such as vitamin D, glucocorticoids, sex steroids, and thyroid hormones; and polypeptide growth factors such as insulin growth factors-I and II. (Canalis, 1993)

The stromal marrow system, located in the medullary cavity (stromal compartment) of bones, is known to be a source of osteoprogenitor cells (Owen and Friedenstein, 1988; Benayahu et al., 1989; Wientroub et al., 1989;). However, there is little information concerning the regulation of osteogenesis within the medullary cavity of bones. It is hypothesized that the so-called local factors act as stimulators and/or inhibitors in the regulation the stromal compartment. These factors may promote or, alternatively, inhibit the differentiation and maturation of osteogenic cells, such as osteoblasts, towards full expression thereby leading to bone formation only at locally restricted sites having contact with the local factors.

Bone remodeling and relative changes in marrow fat have been suggested to be important in the etiology of several forms of osteoporosis. It has been demonstrated that bone formation is deficient when adjacent to fatty marrow. Bone appositional rate and the percentage of bone forming surfaces are reduced in trabecular bone remodeling in close proximity to fatty marrow (Wronksi et al., 1991). The percentage of marrow volume occupied by fat cells has been reported to increase in human senile and postmenopausal osteoporosis (Meunier et al., 1971;) and has been shown to increase with age (Dunnill et al., 1967; Schroder and Touqaard, 1977). A study of patients with displaced intracapsular femoral fractures showed that in most patients with osteoporosis, the hemopoietic tissue was replaced by fat cells (Earney and Earneym, 1972; Eventov et al., 1991). A similar phenomenon can be caused by ovariectomy (Tabuchi et al., 1986), which also has been shown to lead to increased marrow fat volume.

Identification of the mechanisms involved in osteogenic differentiation and the renewal processes are crucial for the understanding of bone physiology and skeletal disorders, such as osteoporosis. These disorders may involve deficient bone formation due to defective maturation of putative osteoblastic progenitors.

Therefore, in order to more clearly understand osteogenic differentiation, an understanding of the cells and factors involved in the mechanisms of osteogenesis is crucial. Additionally, in order to be able to manipulate or modulate the osteogenic process, it would be particularly advantageous to be able to modify bone forming cells, such as osteoblasts, in order to alter or restore their function or to inhibit the action of the regulation factors expressed by stromal bone marrow cells like adipocytes.

The present invention not only provides a method and regulation factors for modifying bone forming cells, it provides a method by which the understanding of osteogenesis is furthered. That is, the present invention extends the knowledge on the intra-stromal interactions affecting the osteogenic expression. Additionally, the present invention provides a method for inhibiting the action of the regulation factors on bone cells. The present invention further provides a method for detecting bone formation disorders. The present invention further can serve as a model to study the cellular interactions that occur in the marrow stroma both in vitro and in situ between the bone marrow cells and bone forming cells.

SUMMARY OF THE INVENTION AND ADVANTAGES

According to the present invention, there is provided regulation factors and a method for modulating bone cells by collecting regulation factors expressed from stromal cells including bone marrow adipocytes and treating the bone forming cells with the regulation factors derived from bone marrow adipocytes and other stromal cells to modify the bone forming cells. A method is also provided for the inhibition of the effects of the regulation factors on bone cells. A method is also provided for detecting bone formation disorders.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
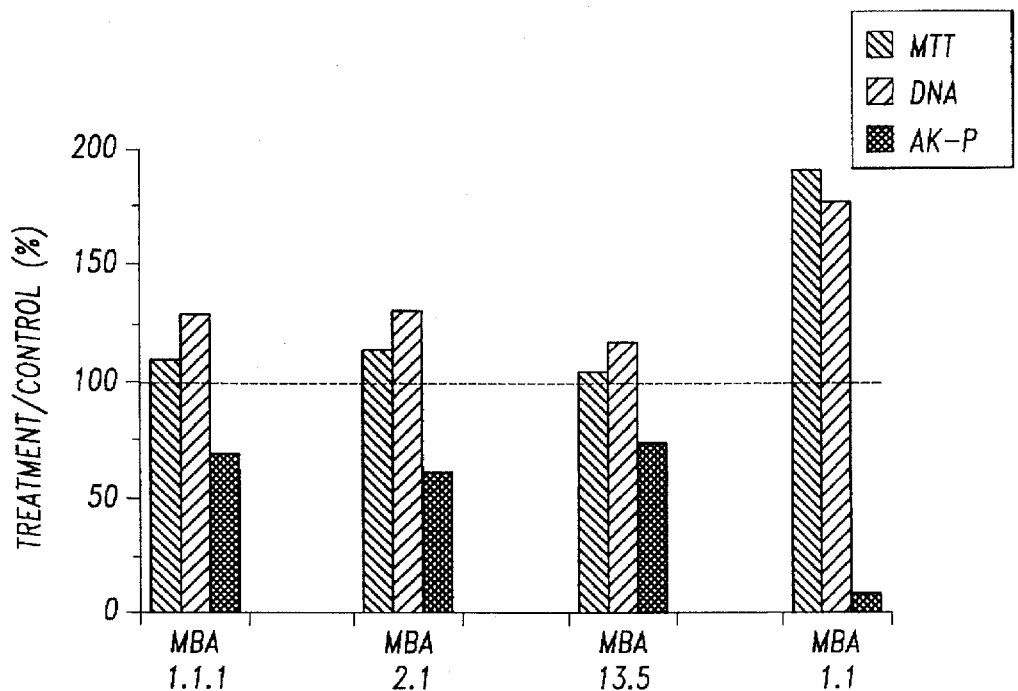
FIG. 1 is a graph illustrating the effects of 10% CM harvested from the various marrow stromal cell lines (MBA series) on growth (MTT, DNA content) and alkaline phosphatase enzymatic activity of MBA-15 cells wherein each column represents the average of triplicate of determinations from 4–6 wells with differences in results not exceeding 10% of variance.

The present invention provides regulation factors and a method for modulating bone forming cells by collecting regulation factors expressed from bone marrow adipocytes and other marrow stromal cells and treating the bone forming cells with the regulation factors derived from bone marrow adipocytes and other stromal cells or with inhibitors of the regulation factors to modify the bone forming cells. That is, the present invention provides a method in which regulation factors expressed from stromal bone marrow adipocytes and other stromal cell types are used to modulate bone forming cells such as osteoblasts. [Benayahu et al. Biochemical and Biophysical Research Communications 1993].

The bone marrow adipocytes and other stromal cell types referred to in the present invention are those bone marrow cells found in the marrow within the skeleton.

By the term "bone forming cells", it is meant the cells which are involved in the formation of bone and/or bone matrix. Typical bone cells include osteoblasts, lining cells, osteocytes, and other cells types of osteogenic lineage.

By the term "modulating bone forming cells", it is meant that changes in various cellular functions of the bone forming cells can be induced or inhibited by exposing the bone forming cells to regulation factors expressed by the bone marrow adipocytes. In other words, application of the regulation factors expressed by the bone marrow adipocytes and other marrow stromal cells types to the bone forming cells can cause or elicit changes in the bone cells.

The factors which are expressed or secreted from bone marrow adipocytes and other stromal cells types can be used for treating bone forming cells in order to modify various cells functions such as expression of alkaline phosphatase, initiation of bone cell proliferation, cellular morphology, and production of extra-cellular matrix constituents which modulate responses to hormones, cytokines, and growth factors. The regulation factors of the bone marrow adipocytes and other stromal cell types are exogenously expressed into the medium surrounding the adipocytes and other stromal cells and can also be found in the circulatory system. In other words, the regulation factors can be either soluble and secreted into medium surrounding the cells, i.e., the medullary compartment or the regulation factors can be bound to an extra-cellular matrix component and being bound to a cell membrane. By either of these mechanism, target bone cells can be exposed to a regulation factor. Because of the solubility of certain of the regulation factors, they are readily dissolved in aqueous solution, the soluble regulation factors can be disseminated both remotely and locally within or beyond the medullary compartment. Therefore, the soluble regulation factors can elicit effects in the bone matrix as well.

The regulation and inhibitory factors can be isolated and purified by established purification techniques known in the art.

By treating bone forming cells with regulation factors derived from bone marrow adipocytes and other stromal cell types in order to modulate the bone forming cells, it is possible to both physically and chemically alter the expression and regulation of the bone forming cells. That is, by treating normal or dysfunctional bone forming cells, it is possible to prevent bone growth in order to restore normal function or to restore the balance of bone formation and bone resorption.

The ability to inhibit the effects of the regulation factors can have far reaching effects in terms of restoring normal function or balance in bone remodeling can have specific application in the treatment of conditions or bone diseases such as osteoporosis. Since there is a high correlation between clinical conditions such as osteoporosis/osteopenia and increased amounts of fatty marrow, in order to reduce or inhibit the effects of the regulation factors expressed by the fatty marrow and treat these conditions, inhibitors of these factors can be administered. This can be accomplished by introducing into either the blood stream or directly into the bone, a solution containing inhibitors of the regulation factors. The inhibitors can be any type of compound which can block the effects of the regulation factors on bone cells such as antibodies, competitive inhibitors, and non-competitive inhibitors.

The regulation factors or the inhibitors of the regulatory factors are administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art.

In the method of the present invention, the regulation factors or their inhibitors can be administered in various ways. It should be noted that the regulation factors can be administered as the compound or as pharmaceutically acceptable salt and can be administered alone or in combination with pharmaceutically acceptable carriers. The compounds can be administered orally, subcutaneously or parenterally including intravenous, intraarterial, intramuscular, intraperitoneally, intramedullary, intraosseous, and intranasal administration. Implants of the compounds are also useful. The patient being treated is a warm-blooded animal and, in particular, mammals including man.

When administering the regulation factors or their inhibitors parenterally, the regulation factors will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the regulation factors can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

A pharmacological formulation of the regulation factors or the inhibitors utilized in the present invention can be administered orally to the patient. Conventional methods such as administering the compounds in tablets, suspensions, solutions, emulsions, capsules, powders, syrups and the like are usable. Known techniques which deliver the regulation factors orally or intravenously and retain the biological activity are preferred.

According to the present invention there is provided a method for diagnosing and detecting bone formation disorders such as osteoporosis. The method for diagnosing and detecting bone formation disorders is carried out by first obtaining a sample from a patient. The sample can be any tissue or bodily fluid which contains markers or factors indicative of the inhibition of bone formation. The preferred samples include either a blood, serum, urine, or a bone marrow samples. The sample is then analyzed for the presence of factors which inhibit bone formation. Analysis for the inhibition factors can be carried out by techniques well known in the art such as radioimmunoassay (RIA) or enzyme linked immunosorbent assay (ELISA). Additionally, bone marrow stromal cell function as well as inhibitory factor levels can be measured using techniques such as immunochemistry and histochemistry which are well known in the art.

The method can also include comparison of the relative amounts of the factors which inhibit bone formation to indicators of bone formation in order to determine if any imbalance between bone remodeling and bone resorption.

The above discussion provides a factual basis for the use or inhibition of regulating factors isolated from bone marrow adipocytes and other stromal marrow cell types for modulating bone forming cells. The methods used with and the utility of the present invention can be shown by the following examples.

EXAMPLES

GENERAL METHODS:

Cell lines and culture conditions: Mouse bone marrow-derived stromal cell lines (MBA series). MBA-2.1 endothelial-like, MBA-1.1.1 and MBA-13.5 fibroblastoid, 14F1.1 adipocytes, MBA-15 osteoblastic cell line (Benayahu et al., 1989; Benayahu, et al., 1991) were seeded in tissue culture plates (Nunc, Denmark) in Dulbecco's Modified Eagles Medium (DMEM) (Bet-Hamek, Israel) with high glucose contents supplemented with 10% fetal calve serum (FCS) (Bio-Lab, Israel). Cultures were incubated at 37° C. in a humidified atmosphere of 10% $CO_2$ in air.

Conditioned medium (CM): (A) Clonal MBA stromal cell lines were seeded at $1.5 \times 10^3$ cell/plate into 60 millimeter culture dishes in DMEM with 10% FCS and grown to confluence. The medium was then removed and growth medium was added to the culture dishes for 3–7 days. CM was collected, centrifuged, Millipore filtered (0.45 μm) and stored in small aliquots at −20° C. (B) Serum free-conditioned medium (SF-CM) was harvested from cultures with medium supplemented with Biogro (Bet-Haemek, Israel), collected and stored as described above.

Isolation and Purification of SF-CM: Following exposure to MBA cells, SF-CM was purified by gel filtration fractionation. The SF-CM was applied to a column (Pharamacia) and the column was eluted using phosphate buffered saline (PBS×2 pH 7.2) at a flow rate of 0.3 milliliter/minute.

Growth factors (GF): rh-Bone morphogenic protein 2 (BMP), transforming growth factor β (TGFβ), insulin-like growth factor (IGF-I) and platelet derived growth factors (PDGF) were purchased from Collaborative Research (USA).

Colorimetric assay for cell growth: Cell viability was measured by colorimetric method with MTT, (3-(4,5-dimethylthiazol-2-yl) 2,5-diphenyl tetrazolium bromide (Sigma) (Mosmann, 1983). Results were read in a microplate reader (Molecular Devices Corp., USA) using a test wavelength of 550 nm, with a reference wavelength of 650 nm.

DNA content in cultured cells: The method utilized was based on the enhancement of fluorescence signals detected by a Hoechst 33258, when 2-[2-(4-hydroxphenyl)-6-benzimidazolyl]-6(1-methyl-4-piperazyl]) benzimidazol.3HCL) bind to DNA (Labaraca and Paigen, 1980). Fluorescence was recorded using an SLM 8000 (SLM Instruments Inc.) at 356 nm excitation and 458 nm emission.

Collagen and non-collagenous protein synthesis: Collagen production by confluent cell cultures was determined by measuring the incorporation of [$^3$H]-proline into newly synthesized proteins as described by Postlethwaite et al. (Postlethwaite et al., 1984). The cells were incubated in DMEM containing 2% FCS, 50 μ/ml ascorbic acid and 2μCi/ml L-(2,3-$^3$H)-proline (Amersham, UK) for 24 hours. Samples of supernatant and cell sonicate were used to quantify total newly synthesized [$^3$H]-proline labeled protein production. The amount of non-collagen proteins (NCP) and collagenase digestible protein (CDP) was measured in the second aliquot using protease-free bacterial collagenase form III (Advanced Biofactures, USA).

Alkaline phosphatase activity: Cells seeded at $1 \times 10^4$/ml in 24-well plates (Nunc) were used for the determination of alkaline phosphatase activity. Enzyme activity was quantitatively measured and correlated to the amount of protein as previously described (Benayahu et al., 1989). Enzyme and protein determinations were performed in microwell plates and read by microplate reader (Molecular Devices Corp., USA).

Various cell lines from marrow stroma (MBA series) classified according to their morphological, biochemical, and biological properties (Benayahu et al., 1989; Benayahu, et al., 1991; Zipori, 1990) were analyzed for their effects on the proliferation and the differentiation of marrow osteoblastic cells in order to ascertain knowledge on the intra-stromal interactions affecting the osteogenic expression. The ability of these stromal cell lines to modulate growth, extracellular matrix production and alkaline phosphatase activity of MBA-15, a marrow-derived osteoblastic cell line (Benayahu, et al., 1989; Benayahu, et al., 1991) was analyzed.

It should be noted that unless otherwise specified, the tissue culture techniques employed art those well known to those skilled in the art.

MBA-15 cells were treated in conditioned media (CM) derived from 14F1.1 bone marrow adipocytes. By the term conditioned media, it is meant that the media has been previously used to grow the 14F1.1 adipocytes in cell culture and then has been filtered to remove cells and other contaminants while allowing the regulation factors to remain. It was found that the 14F1.1 CM effects both the cellular proliferation and differentiation of the marrow osteoblastic MBA-15 cell line. MBA-15 cells were exposed to 14F1.1 CM for five days and marked growth stimulation by 14F1.1 CM was measured by MTT assay and DNA content analysis as shown in FIG. 1.

Figure 2:
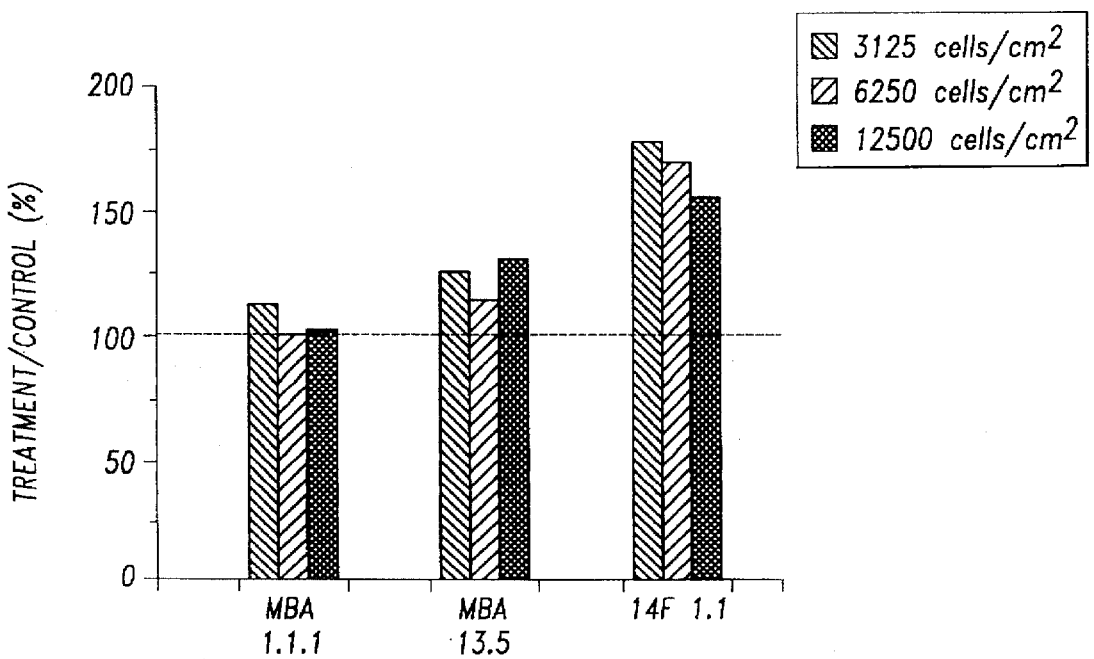
FIG. 2 is a graph illustrating the effects of CM harvested from MBA-1.1.1, MBA-13.5 and 14F1.1 cell lines on MBA-15 cell growth (MTT) when seeded at various initial densities wherein each column represents the average of triplicate determination from 5 wells which differ up to 10% of variance.

In order to eliminate the possibility that the initial cell density of MBA-15 affects the growth response, initial growth densities were varied. As shown in FIG. 2, initial cell density did not alter the cell growth pattern.

In addition to effecting both cellular proliferation and differentiation, 14F1.1 CM also effected stimulation of cell growth with an accompanying suppression of alkaline phosphatase activity in the MBA-15 cells, while CM harvested from other stromal cell lines did not affect these activities to the same extent (FIG. 1).

Figure 3:
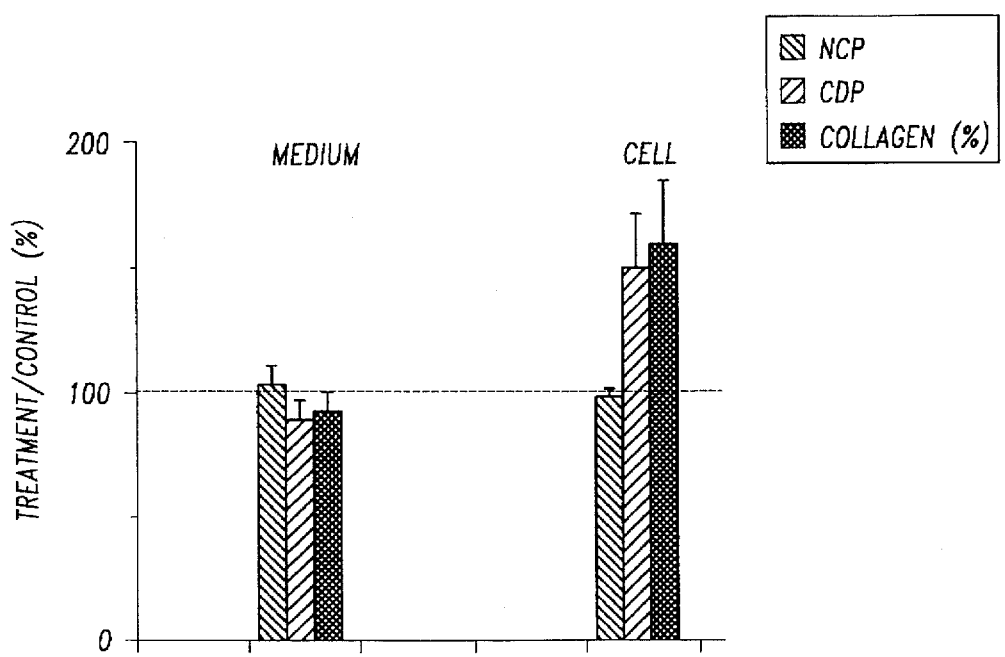
FIG. 3 is a graph illustrating extracellular matrix protein synthesis by MBA-15 cells grown in the presence or absence of 14F1.1 CM following 24 hours of [$^3$H] proline labeling, non-collagenous proteins (NCP) and collagen (CDP) were determined in medium culture and cell layer fraction and wherein the values represented are means±SEM of duplicate determinations of ten separate cultures for each group, calculated according to Postlethwaite's method (Postlethwaite et al., 1984) and wherein the CM added effect is different ($p<0.05$) (unpaired student's t-test), compared to control level.

Under the same culture conditions previously described, MBA-15 cells were exposed to 14F1.1 CM which resulted in changes in cellular protein production as determined following radiolabeling with [$^3$H]-proline. Increased production of collagenous proteins (CDP)/mg protein was elicited in cultures treated with 14F1.1 CM as compared to untreated cultures; however, there was no change in the amount of non-collagenous proteins (NCP) produced. The results indicated a 60% increase in collagen synthesized in the cell layer fraction but no changes in production were noted in labeled proteins secreted into the culture supernatant fraction (FIG. 3).

Figure 4:
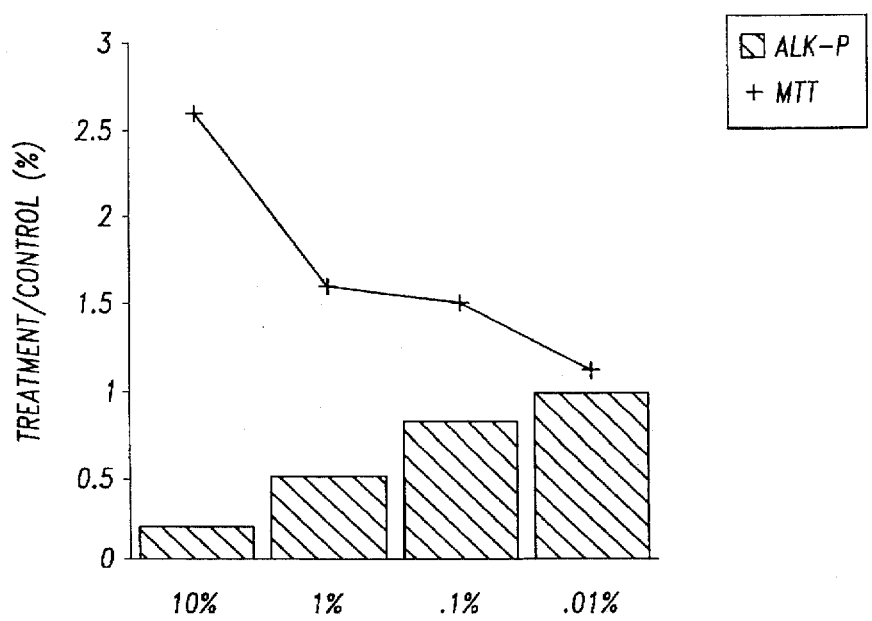
FIG. 4 is a graph illustrating the dose response of affects of 14F1.1 SF-CM Serum Free Conditioned Medium (0.01%–10%) on growth and alkaline phosphatase activity of MBA-15 cells and wherein the results are means of triplicate determination of 4 separate cultures for each point and the difference between wells did not exceed 10% of variance.
Figure 5A:
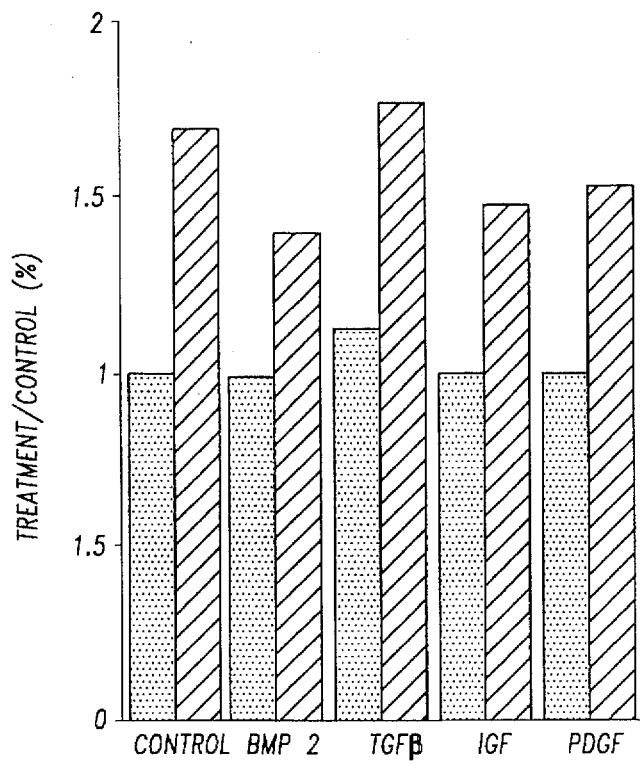
FIG. 5A is a bar graph illustrating the effects of various growth factors on the cell growth of MBA-15 cells in the presence of 1% 14F1.1 SF-CM are represented by (open bars) or in its absence (striped bars) and wherein the results are means of triplicate determinations of four separate cultures for each point with differences between wells not exceeding 10% of variance.
Figure 5B:
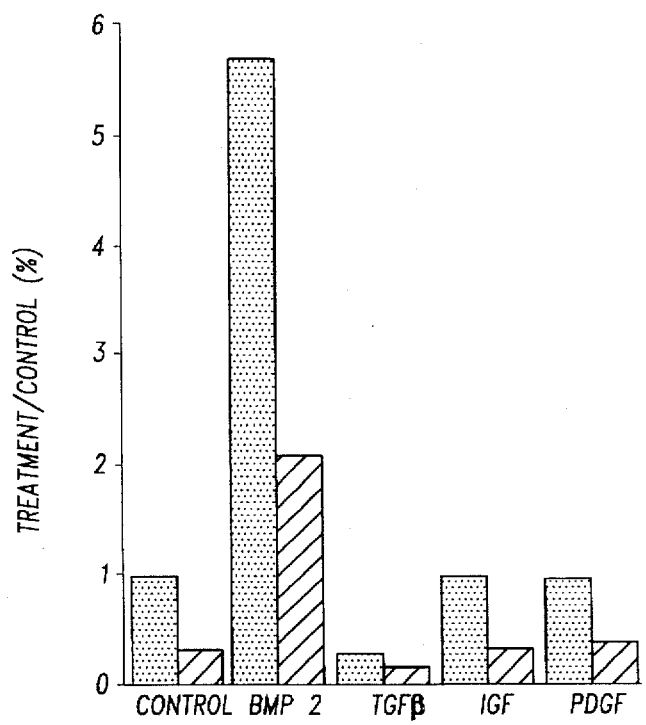
FIG. 5B is a bar graph illustrating the effects of various growth factors on alkaline phosphatase of MBA-15 cells in the presence of 1% 14F1.1 SF-CM are represented by (open bars) or in its absence (striped bars) and wherein the results are means of triplicate determinations of four separate cultures for each point with differences between wells not exceeding 10% of variance.

The effects of MBA-15 enrichment in CM was additionally analyzed under serum-free conditions (SF-CM). 14F1.1 SF-CM fractionated by gel filtration had chemo-physical properties shown in Table 1. 14F1.1 SF-CM caused an increase in MBA-15 cell growth and inhibited alkaline phosphatase activity. A dose dependent relationship between the SF-CM concentrations (0.01%–10%) and the alkaline phosphatase activity was demonstrated (FIG. 4). Since it is known that MBA-15 cells respond to different purified growth factors (Benayahu, et al., 1993), experiments were conducted in order to assess the effects of several known growth factors on MBA-15 cells. These experiments were undertaken to identify the effects of any indigenous cytokines or growth factors in the 14F1.1 SF-CM. The results of these comparisons are shown in FIG. 5 in which the effects of SF-CM compared to various purified growth factors are illustrated. None of the growth factors tested had any effect in altering cell growth (FIG. 5A), but some growth factors did affect alkaline phosphatase activity in MBA-15 cells (FIG. 5B). Specifically, rh-bone morphogenic protein 2 (BMP2 100 ng/ml) increased alkaline phosphatase activity, transforming growth factor β (TGFβ 0.2 ng/ml) decreased enzyme activity, while insulin growth factor (IGF-I 10 ng/ml) and platelet derived growth factors (PDGF 10 ng/ml) had no effect on alkaline phosphatase activity (FIG. 5B).

Comparing the effects of combined exposure of MBA-15 cells to SF-CM with purified growth factors, demonstrated the dominant activity of the SF-CM (FIG. 5).

Figure 6A:
FIG. 6A depicts a confluent growth of adipocyte 14F1.1 cells (Ax200)
Figure 6B:
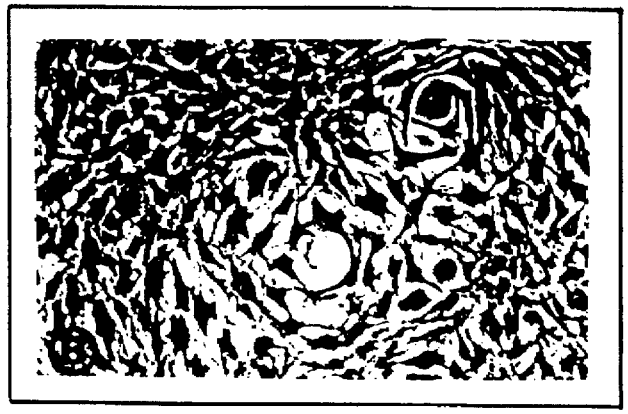
FIG. 6B depicts a confluent growth of normal cuboidal MBA-15 cells prior to treatment with 14F1.1 CM (Bx200)
Figure 6C:
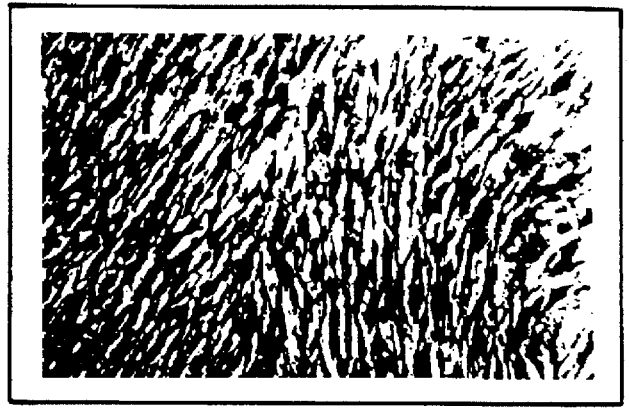
FIG. 6C depicts the fibroblast-like appearance indicative of the morphological changes of MBA-15 cells cultured in the presence of 14F1.1 CM (Cx200)
Figure 7A:
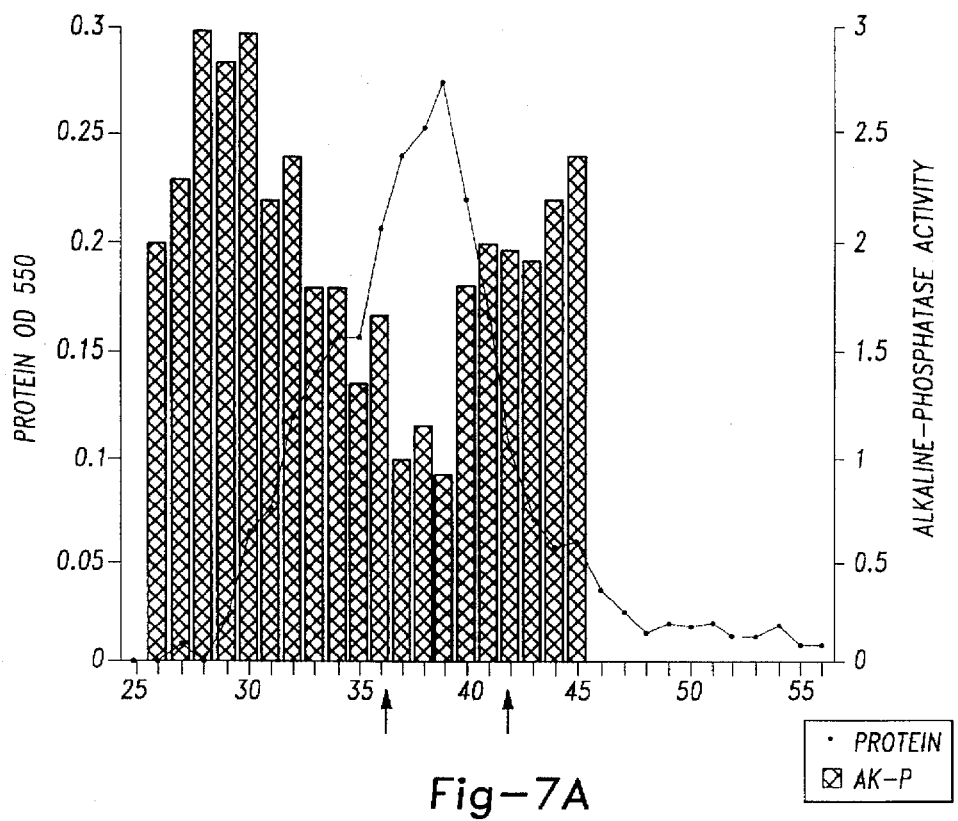
FIG. 7A depicts fractionation of SF-CM by gel filtration, arrows indicate markers of elution (tube 37 represents a 66 kilodalton marker and tube 42 represents a 29 kilodalton marker), wherein the fractions were collected and bioassayed for influence on alkaline phosphatase activity.
Figure 7B:
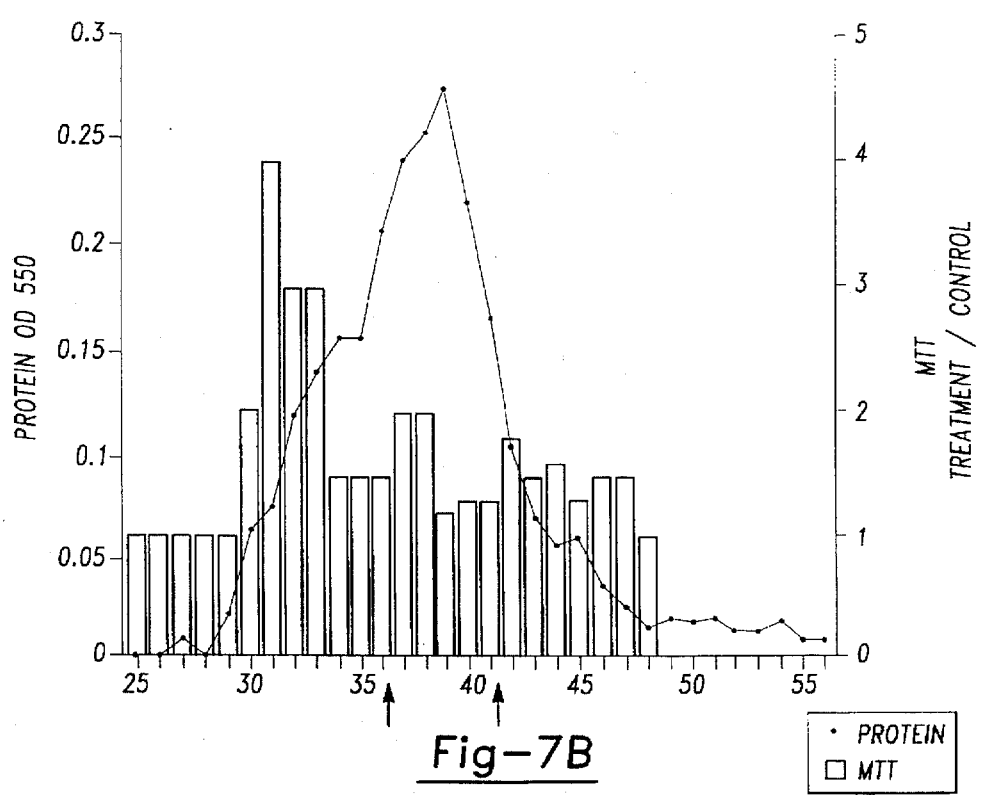
FIG. 7B depicts fractionation of SF-CM by gel filtration, arrows indicate markers of elution (tube 37 represents a 66 kilodalton marker and tube 42 represents a 29 kilodalton marker), wherein the fractions were collected and bioassayed for influence on cell growth using MTT.

Treatment of the bone forming cells (MBA-15) also demonstrated that treatment with the soluble growth regulating factors of the 14F1.1 CM could modulate or cause significant morphological changes in the MBA-15 cell. Along with the changes in cell growth, collagen matrix synthesis, alkaline phosphatase activity, MBA-15 cells treated in the presence of 14F1.1 CM was accompanied by distinct morphological changes. For example, the mosaic outline of MBA-15 cell layer at confluence (FIG. 6B) changed following exposure the MBA-15 cells to 14F1.1 CM. The cellular morphology changed from that of large cuboidal cells into fibroblast-like cells with long processes and slender shapes (FIG. 6C).

These experiments demonstrate that the regulation factors expressed by marrow adipocytes and other stromal cell types are different from the other well known factors, such as IL-1, transforming growth factor β, insulin growth factor (IGF-I) and platelet derived growth factors (PDGF), and that the regulation factors are capable of inducing significant modification of bone forming cell morphology, proliferation, and alkaline phosphatase activity and changes in the extracellular matrix components as well.

Throughout this application various publications are referenced by citation or number. Full citations for the publications referenced by number are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Ascenzi, A., Bonucci, E., Riopamonti, A. and Roveri, N. (1978). *X-ray Calcif. Tiss. Res.* 35,133–143.

Benayahu, D., Kletter, Y., Zipori, D. and Wientroub, S. (1989). "Bone Marrow-Derived Stromal Cell Line Expressing Osteoblastic Phenotype In Vitro and Osteogenic Capacity In Vivo" *J. Cell. Physiol.* 140, 1–7.

Benayahu, D., Fried, A., Zipori, D. and Wientroub. S. (1991). *Calcif. Tissue Int.* 49,202–207.

Benayahu, D., Fried A., Shemay A., Cunningham N., Blumbery S., Wientroub S., (1993). (Submitted).

Burnell, J. M., Baylink, D. J., Chestnut, D. H., Mathews, M. W., and Teubner, E. J. (1982). *Metabolism* 31,1113–1120.

Canalis, E. (1993) "Regulation of Bone Remodeling" in *Primer on the Metabolic Bone Diseases and Disorders of Mineral Metabolism,* 2nd ed., editor Murray J. Fayus, Raven Press, New York.

Dunnill, M. S., Anderson, J. A. and Whitehead, R. (1967). *J. Pathol. Bacteriol.* 94,275–291.

Earney, W. W. and Earneym, A. J. (1972). *J. Am. Geriatr. Soc.* 20, 174–177.

Eventov, I., Frisch, B., Cohen, Z. and Hammel, I. (1991). *Bone* 12, 1–6.

Katsuyuki, F., Kubok, Y. and Sasaki, S. (1976). *Gerentology* 22,363–370.

Labaraca, C. and Paigen, K. (1980). *Anal. Biochem.* 102, 344–352.

Lanntte, M., Scott, D., Dexter, T. M. and Allen, T. D. (1982). *J. Cell. Physiol.* 111,177–186.

Martin, R. B., Chow, B. D. and Lucas, P. A. (1990). *Calcif. Tissue Int.* 46,189–194.

Martin, R. B., Pickett, J. C. and Zinaich, S. (1980). *Clin. Orthop. Rel. Res.* 149,268–282.

Mazess, R. B. (1982). *Clin. Orthop. Rel. Res.* 165, 239–252.

Meunier, P., Courpon, P., Edouard, C., Bernard, J., Brinuier, J., and G. Vignon. (1972). *Clin. Endocrinol. Metab.* 2,239–256.

Mosmann, T. (1983). *J. Immuenel Method.* 66,55–63.

Meunier, P., Aaron, J., Edouard. C. G. Vignon, G. (1971). *Clin. Orthop. Rel. Res.* 80,147–154.

Orbant, K. J. and Odselius, R. (1986). *Calcif. Tiss. Int.* 39,8 10.

Owen, M. and Friedenstein, A. J. (1988). In *Cell and Molecular Biology of Vertebrate Hard Tissue.* Vol. 136 (ed. Evered D. and S. Harnett). pp.42–60. Ciba Fdn. Symp. John Wiley & Sons.

Postlethwaite, A. E., Smith, G. N., Mainardi, C. L., Seyer, J. M. and Kang, A. H. (1984). *J. Immunol.* 132,2470–2477.

Riggs, B. L., Wahner, H. W., Seeman, E., Offord, K. P., Dunn, W. L., Mazess, R. B., Johnson, K. A. and Melton, L. J. (1982), *J. Clin. Invest.* 70,716–723.

Robb, R. A., and Jowsey, J. (1978). *Calcif. Tiss. Res.* 25,265–272.

Schroder, U. and Touqaard, I. (1977). *Acta Pathol. Microbiol Scand. Sec. A.* 84, 559–560.

Simmons, E. D., Pritzker, K. P. H. Grynpas, M. D. (1991). *J. Orthop. Res.* 9,155–167.

Strandth, J. and Norlen, H. (1965). *Acta Orthop. Scand.* 35,257–263.12.

Tabuchi, C., Simmons, D. J., Fausto, A., Russel, S. E., Binderman, I. and Aviolo, L. V. (1986). *J. Clin. Invest.* 78,637–642.

Wronski, T. J., Yen, C. F. and Scott K. S. (1991), *J. Bone Mio. Res.* 6,387–394.

Zipori, D. (1990). *Cancer Cells* 2,205–211.

TABLE 1

| | |
|---|---|
| Temperature Stability | several weeks at 4° C., 20° C., and −70° freeze and thaw |
| Heat Inactivation | 56° C. for 10 minutes |
| | 100° C. for 1 minute |
| Active Following | 50 mM, pH 5 acetate buffer |
| Dialysis and Stability | 50 mM, pH 6 Mess buffer |
| to Buffers | 50 mM, pH 7 phosphate buffer |
| | 50 mM, pH 7.4 Tris buffer |

What is claimed is:

1. A method for stimulating osteoblasts, said method comprising the steps of:
   collecting conditioned medium from bone marrow stromal adipocyte cell cultures;
   treating the osteoblasts with an effective amount of the conditioned medium derived from the adipocytes.

2. A method as set forth in claim 1 wherein said collecting step is further defined as culturing the adipocytes in a suitable growth supporting medium.

3. A method as set forth in claim 1 wherein the medium decreases alkaline phosphatase expression in the osteoblasts.

4. A method as set forth in claim 1 wherein the medium stimulates proliferation of the osteoblasts.

5. A method as set forth in claim 2 wherein said suitable growth supporting medium is serum free.

* * * * *